(12) United States Patent
Robinson et al.

(10) Patent No.: US 11,167,074 B2
(45) Date of Patent: Nov. 9, 2021

(54) SYSTEMS AND METHODS FOR TREATING A TISSUE SITE USING ONE MANIFOLD AND MULTIPLE THERAPY UNITS

(71) Applicant: KCI Licensing, Inc., San Antonio, TX (US)

(72) Inventors: Timothy Mark Robinson, Shillingstone (GB); Christopher Brian Locke, Bournemouth (GB); James A. Luckemeyer, San Antonio, TX (US)

(73) Assignee: KCI Licensing, Inc., San Antonio, TX (US)

(*) Notice: Subject to any disclaimer, the term of this patent is extended or adjusted under 35 U.S.C. 154(b) by 665 days.

(21) Appl. No.: 16/080,353

(22) PCT Filed: Jan. 31, 2017

(86) PCT No.: PCT/US2017/015815
§ 371 (c)(1),
(2) Date: Aug. 28, 2018

(87) PCT Pub. No.: WO2017/160412
PCT Pub. Date: Sep. 21, 2017

(65) Prior Publication Data
US 2019/0046699 A1    Feb. 14, 2019

Related U.S. Application Data

(60) Provisional application No. 62/309,892, filed on Mar. 17, 2016.

(51) Int. Cl.
*A61M 1/00* (2006.01)
*B62K 11/00* (2006.01)
(Continued)

(52) U.S. Cl.
CPC ............ *A61M 1/75* (2021.05); *A61M 1/90* (2021.05); *B62K 11/007* (2016.11); *G01C 19/04* (2013.01);
(Continued)

(58) Field of Classification Search
CPC ........ A61M 1/73; A61M 1/75; A61M 1/0023; A61M 1/60; A61M 1/71; A61M 1/74;
(Continued)

(56) References Cited

U.S. PATENT DOCUMENTS 1,355,846 A   10/1920   Rannells
2,547,758 A   4/1951    Keeling
(Continued)

FOREIGN PATENT DOCUMENTS

AU   550575 B2   3/1986
AU   745271 B2   3/2002
(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
(Continued)

*Primary Examiner* — Susan S Su

(57) ABSTRACT

Systems, apparatuses, and methods for utilizing a dressing having a single manifold fluidly coupled to at least two therapy units in a negative-pressure therapy and/or instillation therapy environment as set forth herein. In one example embodiment wherein the therapy system comprises two therapy units, apparatus and methods may be utilized for alternately applying pressure or fluids to a single tissue site to more quickly remove large amounts of fluid from the tissue site.

40 Claims, 6 Drawing Sheets

(51) Int. Cl.
  *G01C 19/04* (2006.01)
  *B60W 10/20* (2006.01)
(52) U.S. Cl.
  CPC .......... *A61M 1/73* (2021.05); *A61M 2205/16* (2013.01); *A61M 2205/17* (2013.01); *B60W 10/20* (2013.01)
(58) Field of Classification Search
  CPC .......... A61M 1/77; A61M 1/772; A61M 1/80; A61M 1/84; A61M 1/89; A61M 1/90
  See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A * | 12/1987 | McNeil ............. A61M 1/74 604/67 |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2010/0160871 A1* | 6/2010 | Seegert ............. A61F 13/00068 604/290 |
| 2013/0138035 A1* | 5/2013 | Huculak ............. A61M 1/74 604/28 |
| 2014/0163491 A1 | 6/2014 | Schuessler et al. |
| 2015/0073363 A1* | 3/2015 | Kelch ............. A61M 1/73 604/319 |
| 2015/0080788 A1 | 3/2015 | Blott et al. |
| 2015/0320434 A1 | 11/2015 | Ingram et al. |
| 2015/0320603 A1 | 11/2015 | Locke et al. |
| 2016/0256614 A1* | 9/2016 | Hall ............. A61M 1/90 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |

(56) References Cited

FOREIGN PATENT DOCUMENTS

| | | |
|---|---|---|
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al.; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al.; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al.; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al.; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

(56) References Cited

OTHER PUBLICATIONS

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.
International Search Report for corresponding PCT/US2017/015815, dated Jul. 4, 2017.
Written Opinion for corresponding PCT/US2017/015815, dated Jul. 4, 2017.

\* cited by examiner

SYSTEMS AND METHODS FOR TREATING A TISSUE SITE USING ONE MANIFOLD AND MULTIPLE THERAPY UNITS

RELATED APPLICATION

This application claims the benefit, under 35 USC 119(e), of the filing of U.S. Provisional Patent Application No. 62/309,892, entitled "Systems and Methods for Treating a Tissue Site Using One Manifold and Multiple Therapy Units," filed 17 Mar. 2016, which is incorporated herein by reference for all purposes.

TECHNICAL FIELD

The invention set forth in the appended claims relates generally to tissue treatment systems and more particularly, but without limitation, to treating wounds with negative pressure and instillation utilizing a dressing having a single manifold fluidly coupled to multiple therapy units in a negative-pressure and instillation therapy environment.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound can be washed out with a stream of liquid solution, or a cavity can be washed out using a liquid solution for therapeutic purposes. These practices are commonly referred to as "irrigation" and "lavage" respectively. "Instillation" is another practice that generally refers to a process of slowly introducing fluid to a tissue site and leaving the fluid for a prescribed period of time before removing the fluid. For example, instillation of topical treatment solutions over a wound bed can be combined with negative-pressure therapy to further promote wound healing by loosening soluble contaminants in a wound bed and removing infectious material. As a result, soluble bacterial burden can be decreased, contaminants removed, and the wound cleansed.

While the clinical benefits of negative-pressure therapy and/or instillation therapy are widely known, improvements to therapy systems, components, and processes may benefit healthcare providers and patients.

BRIEF SUMMARY

New and useful systems, apparatuses, and methods for utilizing a dressing having a single manifold fluidly coupled to at least two therapy units in a negative-pressure therapy and/or instillation therapy environment are set forth in the appended claims. Illustrative embodiments are also provided to enable a person skilled in the art to make and use the claimed subject matter.

For example, in some embodiments, it is desirable to use multiple therapy units in a therapy system for treating a tissue site where there is so much tissue loss that multiple therapy units are needed to remove fluids from the tissue site at a very high rate and in large volumes and to provide replacement fluids at the same time to manage the wound. In one example embodiment wherein the therapy system comprises two therapy units, for example, apparatus and methods may be utilized for alternately applying pressure or fluids to the tissue site. In another example embodiment wherein the two therapy units each include a canister for collecting fluids from the wound, apparatus and methods may be utilized for controlling the loss of negative pressure when a clinician deactivates one therapy unit to empty fluids from the canister and activates the other therapy unit to continue supplying negative pressure to the tissue site.

More generally, a system for treating a tissue site may comprise a first therapy unit comprising a first pump and a first controller, and a second therapy unit comprising a second pump and a second controller. The system may further comprise a manifold fluidly coupled to the first pump and the second pump and a cover adapted to provide a fluid seal over the manifold and the tissue site. The first controller and the second controller may be adapted to synchronize operation of the first therapy unit and the second therapy unit so that the first pump and the second pump alternately provide negative pressure and/or fluids to the manifold. In one example embodiment, the manifold may be fluidly coupled to the first pump and the second pump at separate locations on the manifold.

More specifically, another example embodiment of a system for treating a tissue site may comprise a first therapy unit comprising a first pump and a first controller and a second therapy unit comprising a second pump and a second controller. The system may further comprise a tissue interface fluidly coupled to the first pump and the second pump and a cover adapted to provide a fluid seal between a therapeutic environment including the tissue site and the tissue interface on one side of the cover and a local external environment the other side of the cover. The first controller and the second controller may be adapted to operate in an intermittent pressure mode to switch the first therapy unit and the second therapy unit on and off between an active state and an inactive state to activate either one of the first pump and the second pump in the active state and deactivate the other one of the first pump and the second pump in the inactive state to provide substantially constant treatment to the tissue interface within the therapeutic environment. The first controller and the second controller may be further adapted to detect a wound pressure (WP) proximate a switching pressure (SP) that is less than the target pressure (TP). The first controller and the second controller may be further adapted to detect a wound pressure (WP) proximate a switching pressure (SP) that is less than the target pressure (TP). The first controller and the second controller may be further adapted to detect a wound pressure (WP) proximate a minimum therapeutic pressure (MTP) less than the switching pressure (SP).

Another example embodiment of a system for treating a tissue site may comprise a first therapy unit including a first controller and a first pump for providing negative pressure and a second therapy unit including a second controller and a second pump for providing negative pressure. The system may further comprise a manifold fluidly coupled to the first pump and the second pump and a cover adapted to provide a fluid seal between a therapeutic environment including the tissue site and the manifold for receiving the negative pressure on one side of the cover and a local external environment the other side of the cover. The first controller and the second controller may be adapted to switch off either one of the first pump and the second pump from a currently active state during an on-cycle and provide an authorization signal after being switched off in response to a reduction of negative pressure in the therapeutic environment while the other one of the first pump and the second pump is in a currently inactive state during an off-cycle.

A method for treating a tissue site is also disclosed and may comprise positioning a manifold at a tissue site and fluidly coupling a first pump of a first therapy unit to the manifold, wherein the first therapy unit includes a first controller, and fluidly coupling a second pump of a second therapy unit to the manifold, wherein the second therapy unit includes a second controller. The method may further comprise covering the manifold with the cover to provide a fluid seal between a therapeutic environment including the tissue site and the manifold on one side of the cover and a local external environment the other side of the cover. The method may further comprise synchronizing operation of the first therapy unit so that the first pump is turned on only when the second pump is turned off, and synchronizing operation of the second therapy unit so that the second pump is turned on only when the first pump is turned off.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
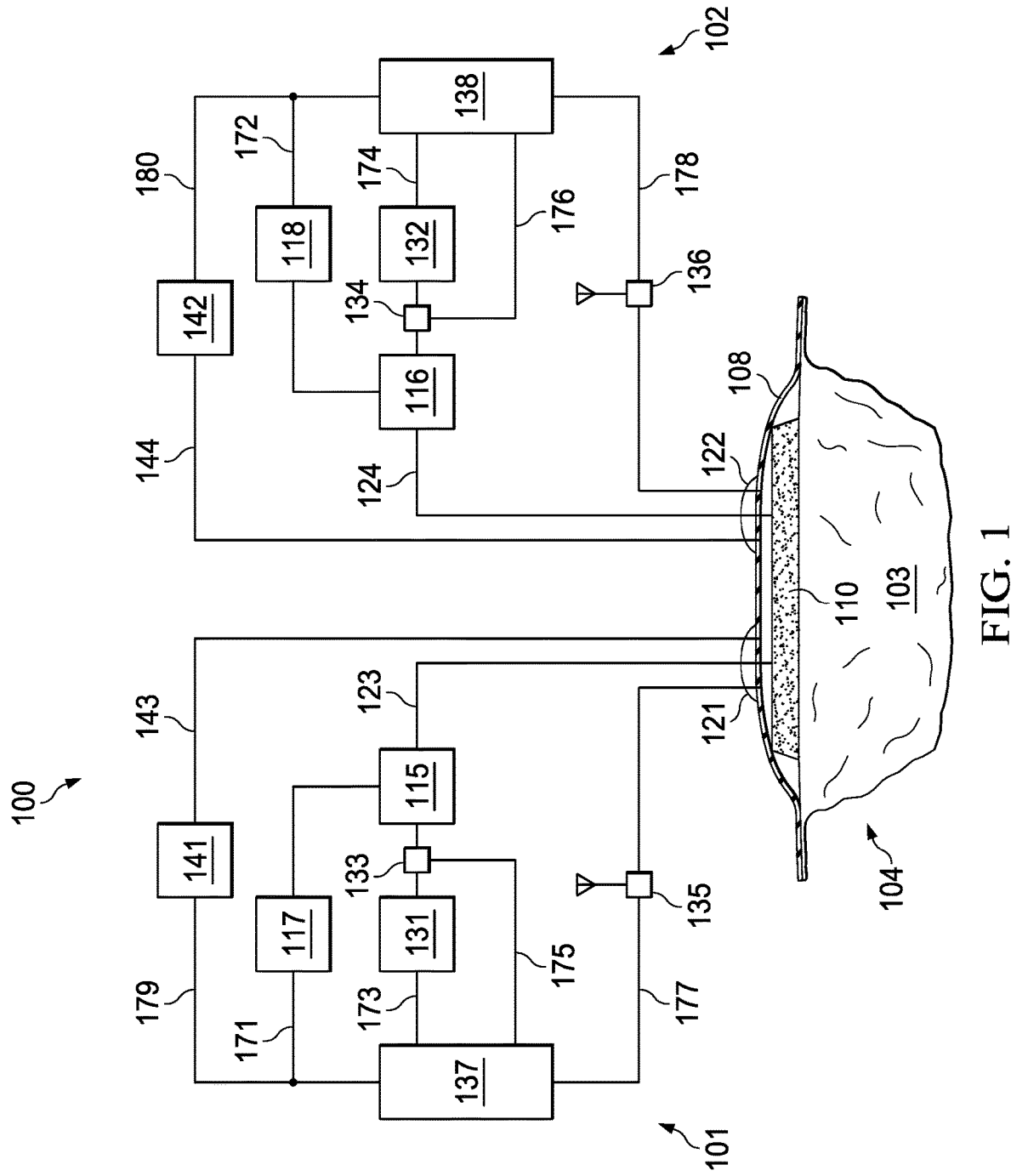
FIG. 1 is a functional block diagram of an example embodiment of a therapy system including a first therapy unit and a second therapy unit that can treat a single tissue site utilizing a dressing having a single manifold fluidly coupled to the therapy units wherein both therapy units alternately apply a wound pressure (WP) to the tissue site in accordance with this specification.

FIG. 1 is a simplified functional block diagram of an example embodiment of a therapy system 100 that may include a first therapy unit 101 and a second therapy unit 102 that can provide negative-pressure therapy with instillation of topical treatment solutions to treat a tissue site 103 in accordance with this specification. The tissue site 103 may include one or more wounds for treatment from the therapy system 100. The therapy system 100 includes a dressing that is coupled to multiple therapy units for treating a tissue site. For example, a dressing, such as a dressing 104, may be fluidly coupled to the therapy units 101 and 102. A dressing generally includes a cover, a tissue interface, and a connector. For example, the dressing 104 may include a cover 108 and a tissue interface 110, wherein the cover 108 is adapted to provide a fluid seal between a therapeutic environment including the tissue site 103 and the tissue interface 110 and on one side of the cover 108, and a local external environment on the other side of the cover 108. A dressing may include a single connector or multiple connectors. The dressing 104, for example, may include a first connector 121 and a second connector 122 fluidly coupling the first therapy unit 101 and the second therapy unit 102, respectively, to the therapeutic environment.

Each of the therapy units may include a negative pressure source, a canister, a pressure sensor, a release valve, an installation source, and a controller electrically coupled to all or a portion of such components. The first therapy unit 101, for example, may include a canister 115 fluidly coupled through a connector 121 via a tube 123 to the therapeutic environment. The first therapy unit 101 may further include and a pressure sensor 117 fluidly coupled to the tissue interface 110 either directly or indirectly through the canister 115. The first therapy unit 101 may also include a second pressure sensor (not shown) that may be coupled or configured to be coupled to the negative-pressure source. The first therapy unit 101, for example, may further include a negative pressure source comprising a negative pressure pump 131 coupled through a pump valve 133 to the canister 115. The first therapy unit 101 may further include a release valve 135 fluidly coupled through the connector 121 to the therapeutic environment. The first therapy unit 101, for example, may further include an instillation source 141 comprising a supply of instillation fluids (not shown) and a negative or positive pressure pump (not shown) fluidly coupled through a tube 143 and the connector 121 to the therapeutic environment. The first therapy unit 101, for example, may further include a controller 137 electrically coupled to the pressure sensor 117, the negative pressure pump 131, the pump valve 133, the release valve 135, and the instillation source 141, either directly or indirectly, via electrical connectors 171, 173, 175, 177 and 179, respectively.

In a similar fashion, the second therapy unit 102, for example, may include a canister 116 fluidly coupled through a connector 122 via a tube 124 to the therapeutic environment. The second therapy unit 102 may further include and a pressure sensor 118 fluidly coupled to the tissue interface 110 either directly or indirectly through the canister 116. The second therapy unit 102 may also include a second pressure sensor (not shown) that and may be coupled or configured to be coupled to the negative-pressure source. The second therapy unit 102, for example, may further include a negative pressure source comprising a negative pressure pump 132 coupled through a pump valve 134 to the canister 116. The second therapy unit 102 may further include a release valve 136 fluidly coupled through the connector 122 to the therapeutic environment. The second therapy unit 102, for example, may further include an instillation source 142 comprising a supply of instillation fluids (not shown) a negative or positive pressure pump (not shown) fluidly coupled through a tube 144 and the connector 122 to the therapeutic environment. The second therapy unit 102, for example, may further include a controller 138 electrically coupled to the pressure sensor 118, the negative pressure pump 132, the pump valve 134, the release valve 136, and the instillation source 142, either directly or indirectly, via electrical connectors 172, 174, 176, 178 and 180, respectively.

In general, components of the therapy system 100 may be coupled directly or indirectly. For example, the negative-pressure pump 131 may be directly coupled to the canister 115 and indirectly coupled to the dressing 104 through the canister 115. Correspondingly, the negative-pressure pump 132 may be directly coupled to the canister 116 and indirectly coupled to the dressing 104 through the canister 116. Components may be fluidly coupled to each other to provide a path for transferring fluids (i.e., liquid and/or gas) between the components. In some embodiments, for example, components may be fluidly coupled through a tube. A "tube," as used herein, broadly refers to a tube, pipe, hose, conduit, or other structure with one or more lumina adapted to convey a fluid between two ends. Typically, a tube is an elongated, cylindrical structure with some flexibility, but the geometry and rigidity may vary. In some embodiments, components may additionally or alternatively be coupled by virtue of physical proximity, being integral to a single structure, or being formed from the same piece of material. Coupling may also include mechanical, thermal, electrical, or chemical coupling (such as a chemical bond) in some contexts. For example, connectors 121 and 122 may be fluidly coupled to tubes 123 and 124, respectively, to provide negative pressure to the dressing 104 from the negative-pressure pump 131 and the negative-pressure pump 132, respectively. The negative pressure developed by a negative-pressure source may be delivered through a tube to a connector, such as the connector 121 and the connector 122. In one illustrative embodiment, a connector may be a T.R.A.C.® Pad or Sensa T.R.A.C.® Pad available from KCI of San Antonio, Tex. A connector may allow the negative pressure to be delivered to a dressing. In other exemplary embodiments, a tube may be inserted through the cover 108 of the dressing 104.

In operation, the tissue interface 110 may be placed within, over, on, or otherwise proximate to a tissue site. The cover 108 may be placed over the tissue interface 110 and sealed to tissue near the tissue site 103, i.e., peri-tissue. For example, the cover 108 may be sealed to peri-tissue adjacent the tissue site 103. Thus, the dressing 104 can provide a sealed therapeutic environment proximate to a tissue site that is substantially isolated from the external environment. The negative-pressure pump 131 and the negative-pressure pump 132 can reduce the pressure in the sealed therapeutic environment provided by the dressing 104. Negative pressure applied across the tissue site 103 through the tissue interface 110 in the sealed therapeutic environment can induce macrostrain and microstrain in the tissue site, as well as remove exudates and other fluids from the tissue site, which can be collected in the canister 115 and the canister 116, respectively, and properly emptied and disposed of when filled. And instillation solution may also be delivered to the therapeutic environment for treating the tissue site.

The fluid mechanics of using a negative-pressure source to reduce pressure in another component or location, such as within a sealed therapeutic environment, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example. In general, exudates and other fluids flow toward lower pressure along a fluid path. Thus, the term "downstream" typically implies a position in a fluid path relatively closer to a negative-pressure source, and conversely, the term "upstream" implies a position relatively further away from a negative-pressure source. Similarly, it may be convenient to describe certain features in terms of fluid "inlet" or "outlet" in such a frame of reference. This orientation is generally presumed for purposes of describing various features and components of negative-pressure therapy systems herein. However, the fluid path may also be reversed in some applications (such as by substituting a positive-pressure source for a negative-pressure source) and this descriptive convention should not be construed as a limiting convention.

The term "tissue site" in this context broadly refers to a wound, defect, or other treatment target located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

"Negative pressure" generally refers to a pressure less than a local ambient pressure, such as the ambient pressure in a local environment external to a sealed therapeutic environment provided by the dressing 104. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −75 mm Hg (−9.9 kPa) and −300 mm Hg (−39.9 kPa).

A negative-pressure source, such as the negative-pressure sources described above, may each include an electrically-powered device that can reduce the pressure in a sealed volume, such as a vacuum pump, e.g., the negative-pressure pumps 131 and 132, a suction pump, a wall suction port available at many healthcare facilities, or a micro-pump, for example. A negative-pressure source may be housed within or used in conjunction with other components, such as sensors, processing units, alarm indicators, memory, databases, software, display devices, or user interfaces that further facilitate therapy. For example, in some embodiments, the negative-pressure source may be combined with the controllers 137 and 138 and other components into a therapy unit. A negative-pressure supply may also have one or more supply ports configured to facilitate coupling and de-coupling the negative-pressure supply to one or more distribution components. A negative-pressure source may also be controlled or regulated by a pump valve coupled to a controller for providing negative pressure to a canister. For example, the pump valves 133 and 134 may be fluidly coupled between the negative-pressure pumps 131 and 132 and the canisters 115 and 116, and electrically coupled to the controllers 137 and 138, to control the application of negative pressure to the tissue site 103 based on a pressure control mode implemented by the controllers 137 and 138.

The tissue interface 110 can be generally adapted to contact a tissue site. The tissue interface 110 may be partially or fully in contact with the tissue site. If the tissue site is a wound or several wounds, for example, the tissue interface 110 may partially or completely fill the wound, or may be placed over the wound. The tissue interface 110 may take many forms, and may have many sizes, shapes, or thicknesses depending on a variety of factors, such as the type of treatment being implemented or the nature and size of a tissue site. For example, the size and shape of the tissue interface 110 may be adapted to the contours of deep and irregular shaped tissue sites. Moreover, any or all of the surfaces of the tissue interface 110 may have projections or an uneven, course, or jagged profile that can induce strains and stresses on a tissue site, which can promote granulation at the tissue site.

In some embodiments, the tissue interface 110 may be a manifold. A "manifold" in this context generally includes any substance or structure providing a plurality of pathways adapted to collect or distribute fluid across a tissue site under pressure. For example, a manifold may be adapted to receive negative pressure from a source and distribute negative pressure through multiple apertures across a tissue site, which may have the effect of collecting fluid from across a tissue site and drawing the fluid toward the source. In some embodiments, the fluid path may be reversed or a secondary fluid path may be provided to facilitate delivering fluid across a tissue site.

In some illustrative embodiments, the pathways of a manifold may be interconnected to improve distribution or collection of fluids across a tissue site. In some illustrative embodiments, a manifold may be a porous foam material having interconnected cells or pores. For example, cellular foam, open-cell foam, reticulated foam, porous tissue collections, and other porous material such as gauze or felted mat generally include pores, edges, and/or walls adapted to form interconnected fluid channels. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

The average pore size of a foam material may vary according to needs of a prescribed therapy. For example, in some embodiments, the tissue interface 110 may be a foam material having pore sizes in a range of 400-600 microns. The tensile strength of the tissue interface 110 may also vary according to needs of a prescribed therapy. For example, the tensile strength of a foam material may be increased for instillation of topical treatment solutions. In one non-limiting example, the tissue interface 110 may be an open-cell, reticulated polyurethane foam such as GranuFoam® dressing or VeraFlo® foam, both available from Kinetic Concepts, Inc. of San Antonio, Tex.

The tissue interface 110 may be either hydrophobic or hydrophilic. In an example in which the tissue interface 110 may be hydrophilic, the tissue interface 110 may also wick fluid away from a tissue site, while continuing to distribute negative pressure to the tissue site. The wicking properties of the tissue interface 110 may draw fluid away from a tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether.

Other foams that may exhibit hydrophilic characteristics include hydrophobic foams that have been treated or coated to provide hydrophilicity.

The tissue interface 110 may further promote granulation at a tissue site when pressure within the sealed therapeutic environment is reduced. For example, any or all of the surfaces of the tissue interface 110 may have an uneven, coarse, or jagged profile that can induce microstrains and stresses at a tissue site if negative pressure is applied through the tissue interface 110.

In some embodiments, the tissue interface 110 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The tissue interface 110 may further serve as a scaffold for new cell-growth, or a scaffold material may be used in conjunction with the tissue interface 110 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 108 may provide a bacterial barrier and protection from physical trauma. The cover 108 may also be constructed from a material that can reduce evaporative losses and provide a fluid seal between two components or two environments, such as between a therapeutic environment and a local external environment. The cover 108 may be, for example, an elastomeric film or membrane that can provide a seal adequate to maintain a negative pressure at a tissue site for a given negative-pressure source. The cover 108 may have a high moisture-vapor transmission rate (MVTR) in some applications. For example, the MVTR may be at least 300 $g/m^2$ per twenty-four hours in some embodiments. In some example embodiments, the cover 108 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained.

An attachment device may be used to attach the cover 108 to an attachment surface, such as undamaged epidermis, a gasket, or another cover. The attachment device may take many forms. For example, an attachment device may be a medically-acceptable, pressure-sensitive adhesive that extends about a periphery, a portion, or an entire sealing member. In some embodiments, for example, some or all of the cover 108 may be coated with an acrylic adhesive having a coating weight between 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

Sensors, such as the pressure sensors 117 and 118, are generally known in the art as any apparatus operable to detect or measure a physical phenomenon or property, and generally provide a signal indicative of the phenomenon or property that is detected or measured. For example, the pressure sensors 117 and 118 may be configured to measure one or more operating parameters of the therapy system 100. In some embodiments, the pressure sensors 117 and 118 may be a transducer configured to measure pressure in a pneumatic pathway and convert the measurement to a signal indicative of the pressure measured. In some embodiments, for example, the pressure sensors 117 and 118 may be a piezoresistive strain gauge. Preferably, the signals from the pressure sensors 117 and 118 are suitable as an input signal to the controllers 137 and 138, but some signal conditioning may be appropriate in some embodiments. For example, the signal may need to be filtered or amplified before it can be processed by the controllers 137 and 138. Typically, the signal is an electrical signal, but may be represented in other forms, such as an optical signal.

The canister 115 and the canister 116 are representative of a container, pouch, or other storage component, which can be used to manage exudates and other fluids withdrawn and collected from a tissue site. In many environments, a rigid container may be preferred or required for collecting, storing, and disposing of fluids from the tissue site. In other environments, fluids may be properly disposed of without rigid container storage, and a re-usable container could reduce waste and costs associated with negative-pressure therapy. In one example embodiment, the canisters 115 and 116 may collect fluids from the tissue site 103 over several hours before the canisters need to be emptied. Having two canisters rather than one canister allows a user or caregiver to empty one canister while the other continues to provide negative pressure to the tissue site and continues to be filled with fluids from the tissue site.

The instillation sources 141 and 142 may include a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, and isotonic solutions. Such solutions may be delivered to the therapeutic environment as described above by gravitational forces regulated by a valve mechanism (not shown) or a pump (not shown) fluidly coupled to a container (not shown) storing the solution, each of which may be controlled by the controllers 137 and 138. In some embodiments, the pump may be a positive pressure pump, such as a peristaltic pump, that forces the solution into the therapeutic environment.

A controller, such as the controller 137 and the controller 138, may be a microprocessor or computer programmed to operate one or more components of the therapy units 101 and 102, such as the negative-pressure sources described above. In some embodiments, for example, the controllers may be a microcontroller, which generally comprises an integrated circuit containing a processor core and a memory programmed to directly or indirectly control one or more operating parameters of the therapy units. Operating parameters may include the power applied to the negative-pressure pumps 131 and 132, the pressure generated by the negative-pressure pumps 131 and 132, or the pressure distributed to the tissue interface 110, for example. The controller 137 and the controller 138 may also be configured to receive one or more input signals, such as a feedback signal or a user-provided signal, and programmed to modify one or more operating parameters based on the input signals. The controller 137 and the controller 138 may also be configured to implement an algorithm such as, for example, a selection of pressure control modes, for providing negative pressure to the tissue site 103.

In one embodiment, the controller 137 and the controller 138 may receive and processes data from the pressure sensor 117 and the pressure sensor 118, such as data related to the pressure distributed to the tissue interface 110. The controllers may also control the operation of one or more components of therapy units to manage the pressure distributed to the tissue interface 110 for application to the tissue site 103. The pressure measured by the pressure sensors 117 and 118 may be representative of the pressure applied to the tissue interface 110 and referred to as the wound pressure (WP). In one embodiment, the controllers may include an input for receiving a desired target pressure (TP) set by a clinician or other user and may be programmed for processing data relating to application of the target pressure (TP) to the tissue site 103 according to a programmed pressure control mode. In one example embodiment, the target pressure (TP) may be a fixed pressure value determined by a user/caregiver as the reduced pressure target desired for therapy at the tissue site 103 and then provided as input to the controllers. The clinician may be a nurse or a doctor or other approved clinician who prescribes the desired negative pressure to be applied to the tissue site 103. The desired negative pressure may vary depending on the physiology of a tissue site including the type of tissue forming the tissue site 103, the type of injury or wound (if any), the medical condition of the patient, and the preference of the attending clinician. After selecting the desired target pressure (TP), the negative-pressure sources may be controlled to approximate the target pressure (TP) applied to the tissue site 103.

Figure 2A:
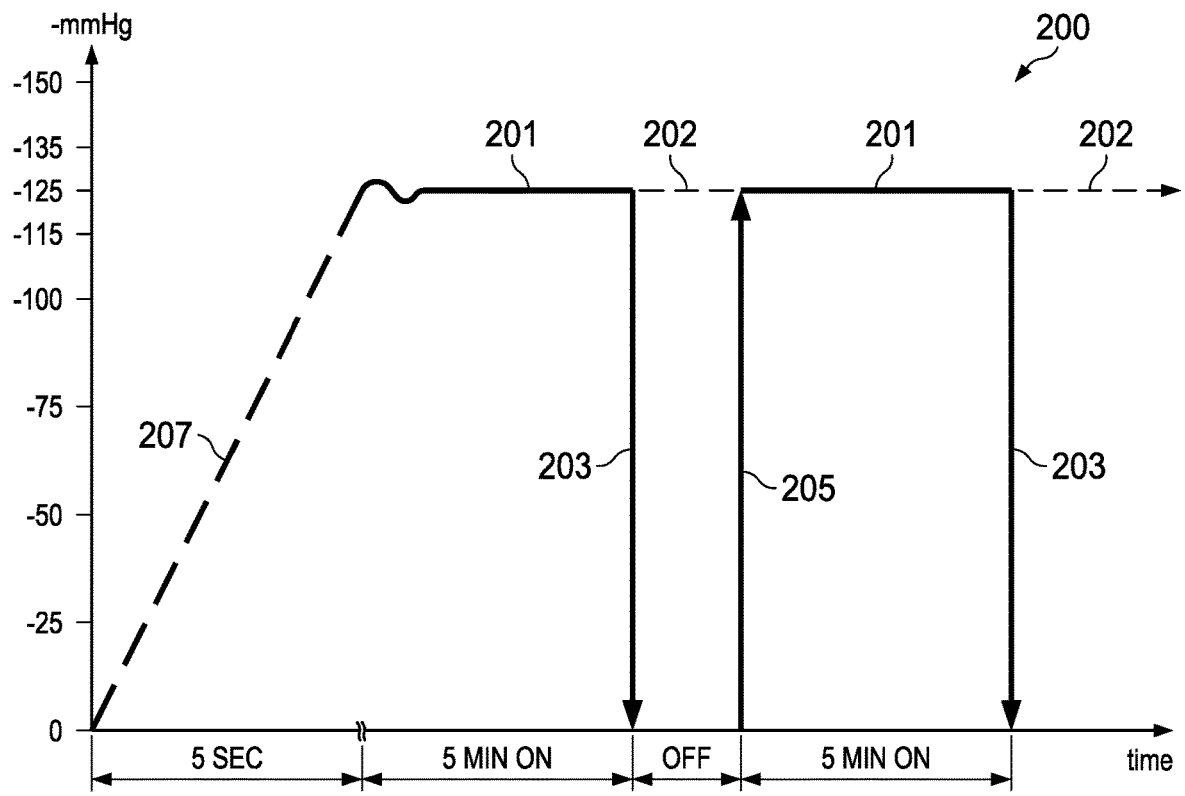
FIG. 2A is a graph illustrating an illustrative embodiment of two pressure control modes for the negative-pressure and instillation therapy system of FIG. 1 wherein the x-axis represents time in minutes (min) and/or seconds(sec) and the y-axis represents pressure generated by a pump in Torr (mmHg) that varies with time in a continuous pressure mode and an intermittent pressure mode that may be used for applying negative pressure in the therapy system.

Referring more specifically to FIG. 2A, a graph illustrates an illustrative embodiment of two pressure control modes 200 that may be used for the therapy units 101 and 102 of FIG. 1. The x-axis of the graph represents time in minutes (min) and/or seconds (sec) and the y-axis of the graph represents pressure generated by a pump in Torr (mmHg) that varies with time. The two pressure control modes 200 illustrated include, for example, pressure generated over time in a continuous pressure mode at a predetermined pressure and pressure generated over time and an intermittent pressure mode between a predetermined pressure and atmospheric pressure that may be used for the application of negative pressure in the therapy system 100 as described above.

In a continuous pressure mode, the target pressure (TP) may be set by the user as indicated by solid lines 201 and dashed lines 202 wherein the wound pressure (WP) is applied to the tissue site 103 until the user deactivates the negative-pressure pumps 131 and 132. In an intermittent pressure mode, the target pressure (TP) may be set by the user as indicated by solid lines 201, 203 and 205 wherein the wound pressure (WP) is cycled between the target pressure (TP) and either a minimum operating pressure (MOP) or atmospheric pressure. For example, the target pressure (TP) may be set by the user at a negative pressure value of 125 mmHg for a specified period of time (e.g., 5 min) followed by the therapy being turned off for a specified period of time (e.g., 2 min) as indicated by the gap between the solid lines 203 and 205. In one embodiment, the negative pressure therapy may be turned off by venting the therapeutic environment surrounding the tissue site 103 to the atmospheric pressure, and then repeating the cycle by turning the therapy back on as indicated by solid line 205. In yet another example embodiment, the target pressure (TP) may be set by the user at a negative pressure value of 125 mmHg for a specified period of time (e.g., 5 min) followed by the therapy being reduced to the minimum operating pressure (MOP) such as, for example, 25 mmHg for a specified period of time (e.g., 2 min). This cycling in the intermittent pressure mode resembles a square wave wherein the negative pressure applied to the tissue site 103 varies between the target pressure (TP) and either the minimum operating pressure (MOP) or the atmospheric pressure.

In some example embodiments, the decrease in the wound pressure (WP) at the tissue site 103 from atmospheric pressure to the target pressure (TP) is not instantaneous, but rather gradual depending on the type of therapy equipment and dressing being used for the particular therapy treatment. For example, the negative-pressure pumps 131 and 132 and the dressing 104 may have an initial rise time as indicated by the dashed line 207 that may vary depending on the type of dressing and therapy equipment being used. The initial rise time for one therapy system may be in a negative pressure range between about 20-30 mmHg/second (about 25 mmHg/second shown) and for another therapy system in a negative pressure range between about 5-10 mmHg/second. As can be seen, the rise time from atmospheric pressure to the target pressure (TP) occurs over a relatively short period of time, e.g., five seconds, compared to the on-cycle of the therapy being applied to the tissue site 103. When the therapy units 101 and 102 are operating in the intermittent mode, the repeating rise time as indicated by the solid line 205 may be a value substantially equal to the initial rise time as indicated by the dashed line 207.

The target pressure may also be a variable target pressure (VTP) controlled or determined by the controller that varies in a dynamic pressure mode. For example, the variable target pressure (VTP) may vary between a maximum and minimum pressure value that may be set as an input determined by a user as the range of negative pressures desired for therapy at the tissue site 103. The variable target pressure (VTP) may also be processed and controlled by the controllers that vary the target pressure (TP) according to a predetermined waveform such as, for example, a sine waveform or a saw-tooth waveform or a triangular waveform. A user also may set these waveforms as an input so that a predetermined negative pressure or time-varying negative pressures may be applied as therapy for the tissue site.

Figure 2B:
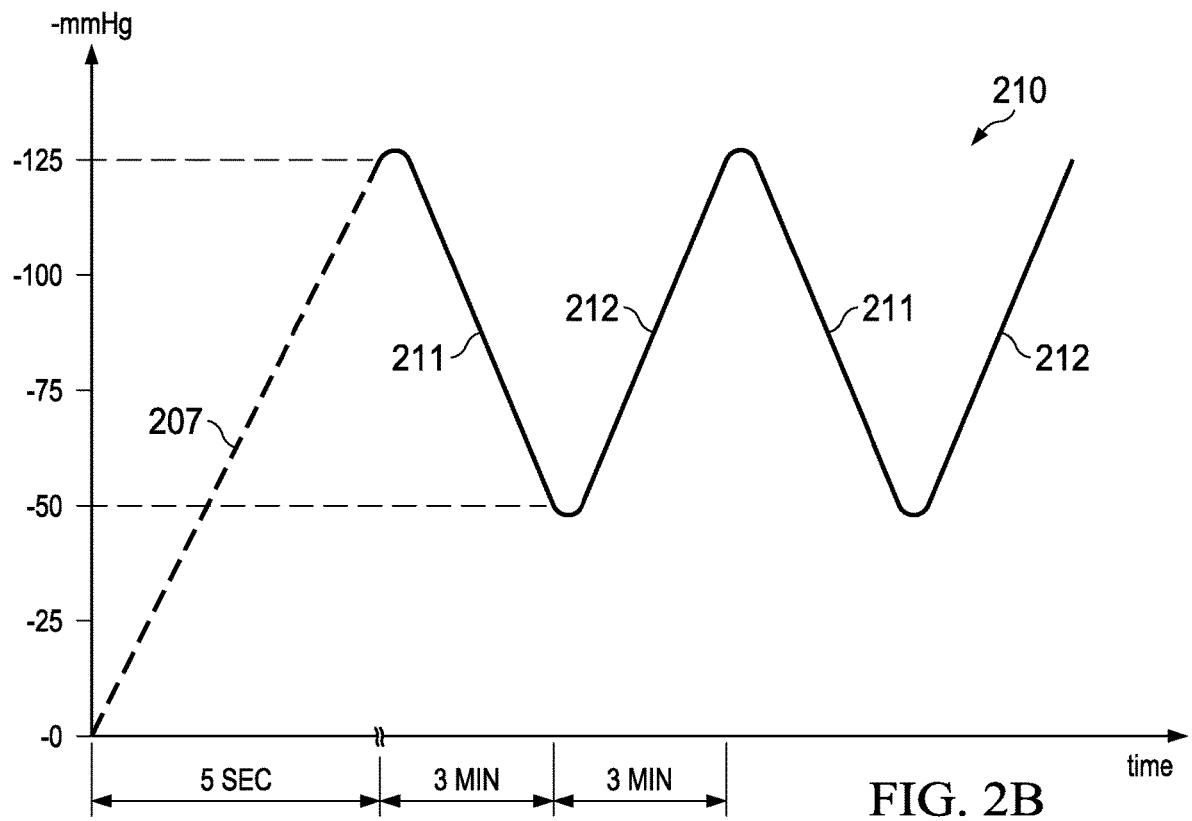
FIG. 2B is a graph illustrating an illustrative embodiment of another pressure control mode for the negative-pressure and instillation therapy system of FIGS. 1 and 1A wherein the x-axis represents time in minutes (min) and/or seconds (sec) and the y-axis represents pressure generated by a pump in Torr (mmHg) that varies with time in a dynamic pressure mode that may be used for applying negative pressure in the therapy system.

Referring to FIG. 2B, a graph illustrating an example embodiment of another type of pressure control mode for the therapy system of FIG. 1 is shown wherein the x-axis represents time in minutes (min) and/or seconds (sec) and the y-axis represents pressure generated by a pump in Torr (mmHg) that varies with time. The pressure control mode illustrated is a dynamic pressure mode 210 that may be used for applying a variable target pressure (VTP) to the tissue site 103. The variable target pressure (VTP) may be applied to tissue site 103 in the form of a triangular waveform varying between a minimum and maximum pressure of 50-125 mmHg with a rise time 212 set at a rate of +25 mmHg/min. and a descent time 211 set at −25 mmHg/min, respectively. In another embodiment of the therapy system 100, the variable target pressure (VTP) may be a negative pressure that applies reduced pressure to tissue site 103 in the form of a triangular waveform varying between 25-125 mmHg with a rise time 212 set at a rate of +30 mmHg/min and a descent time 211 set at −30 mmHg/min. Again, the type of system and tissue site determines the type of reduced pressure therapy to be used.

Figure 3:
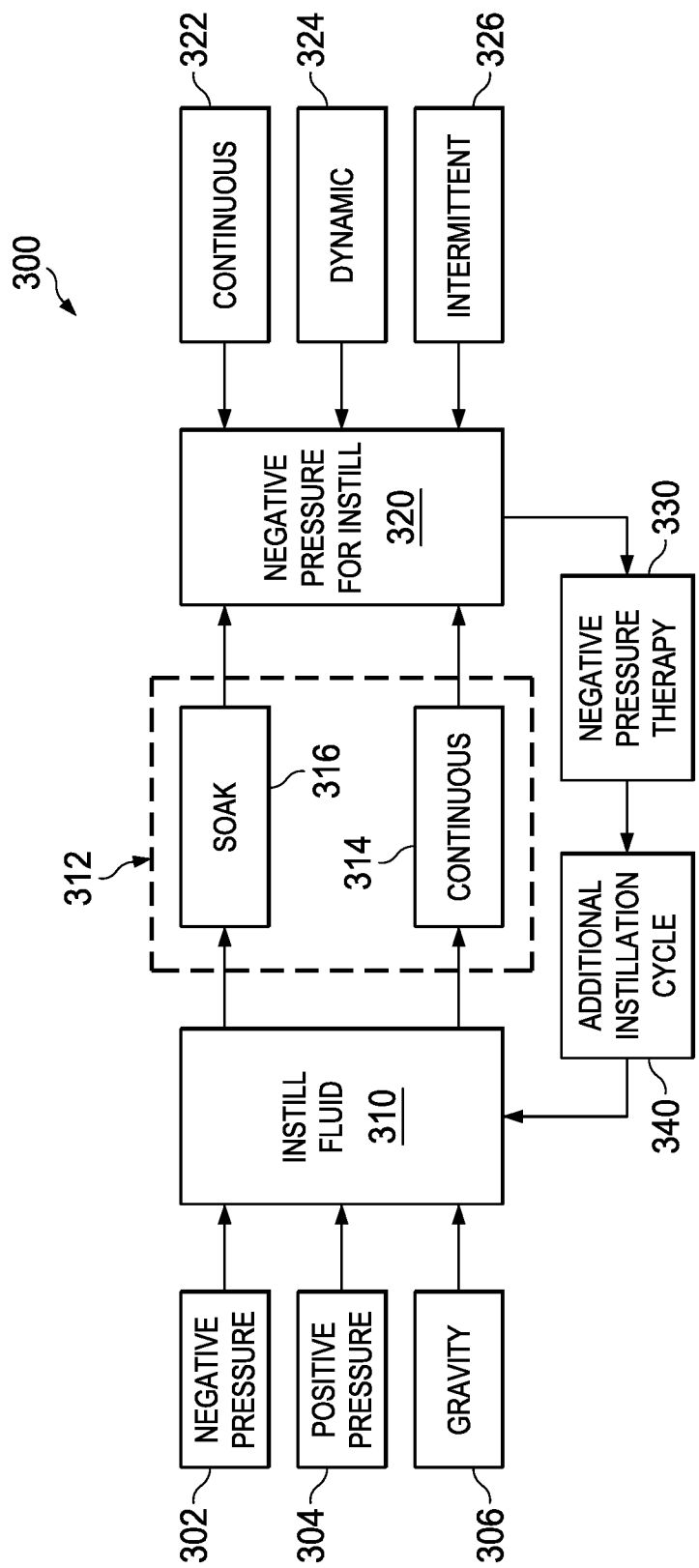
FIG. 3 is a block diagram showing an illustrative embodiment of a therapy method for providing negative-pressure and instillation therapy for delivering treatment solutions to a dressing at a tissue site.

FIG. 3 is a block diagram illustrating an illustrative embodiment of a therapy method 300 that may be used for providing negative-pressure and instillation therapy for delivering an antimicrobial solution or other treatment solution to a dressing at a tissue site. In one embodiment, the controller 137 and the controller 138 receive and process data, such as data related to fluids provided to the tissue interface. Such data may include the type of instillation solution prescribed by a clinician, the volume of fluid or solution to be instilled to the tissue site ("fill volume"), and the amount of time needed to soak the tissue interface ("soak time") before applying a negative pressure to the tissue site. The fill volume may be, for example, between 10 and 500 mL, and the soak time may be between one second to 30 minutes. The controllers may also control the operation of one or more components of the therapy system 100 to manage the fluids distributed from the instillation source 141 and the instillation source 142 for dispensing the fluids to the tissue site 103. In one embodiment, fluid may be instilled to the tissue site 103 by applying a negative pressure from the negative-pressure sources to reduce the pressure at the tissue site 103 to draw the instillation fluid into the dressing 104 as indicated at 302. In another embodiment, fluid may be instilled to the tissue site 103 by applying a positive pressure from a negative-pressure source (not shown) or a positive-pressure source (not shown) to force the instillation fluid into the tissue interface 110 as indicated at 304. In yet another embodiment, fluid may be instilled to the tissue site 103 by elevating the instillation sources to height sufficient to force the instillation fluid into the tissue interface 110 by the force of gravity as indicated at 306. Thus, the therapy method 300 includes instilling fluid into the tissue interface 110 by either drawing or forcing the fluid into the tissue interface 110 as indicated at 310.

The therapy method 300 may control the fluid dynamics of applying the fluid solution to the tissue interface 110 at 312 by providing a continuous flow of fluid at 314 or an intermittent flow of fluid for soaking the tissue interface 110 at 316. The therapy method 300 may include the application of negative pressure to the tissue interface 110 to provide either the continuous flow or intermittent soaking flow of fluid at 320. The application of negative pressure may be implemented to provide a continuous pressure mode of operation at 322 as described above to achieve a continuous flow rate of instillation fluid through the tissue interface 110 or a dynamic pressure mode of operation at 324 as described above to vary the flow rate of instillation fluid through the tissue interface 110. Alternatively, the application of negative pressure may be implemented to provide an intermittent mode of operation at 326 as described above to allow instillation fluid to soak into the tissue interface 110 as described above. In the intermittent mode, a specific fill volume and the soak time may be provided depending, for example, on the type of tissue site 103 being treated and the type of dressing 104 being utilized to treat the tissue site 103. After or during instillation of fluid into the tissue interface 110 has been completed, the therapy method 300 may be utilized using any one of the three modes of operation at 330 as described above. The controllers may be utilized to select any one of these three modes of operation and the duration of the negative pressure therapy as described above before commencing another instillation cycle at 340 by instilling more fluid at 310.

In some circumstances, a patient may be so severely injured that their life is vitally threatened by the size or severity of a wound. One example occurs when a patient has lost so much tissue at one tissue site that multiple therapy units need to be fluidly coupled to a single dressing that is applied to the tissue site to manage the wound. In such cases, fluids and exudates are being removed from the tissue site at a very high rate and large volumes of replacement fluids are being provided at the same time. In such extreme cases, the patient is under acute supervision that often requires the caregiver to constantly change the canisters which is not only a distraction for the caregiver, but also a serious disruption of the therapy being provided to the patient. For example, the caregiver would be required to deactivate the therapy unit and empty the canister every few hours or even more frequently, during which time the wound pressure could be lost or diminished as a result of the dressing leaking pressure or the amount of time it takes the caregiver to replace the canister. In another example, a serious disruption of therapy could occur if a therapy system that typically has only one pump fails and is no longer able to provide negative-pressure therapy to the tissue site. Thus, it is desirable to have a safe and effective therapy system capable of increasing fluid-removal capacity of wound and therapy solutions while also preventing the loss of negative pressure when a canister is being emptied.

Some therapy systems attempt to overcome the problems by using a single therapy unit that has a greater pumping capacity than the standard pumps used in negative-pressure therapy systems. However, negative-pressure therapy systems that use a single larger pump may also suffer from other drawbacks. For example, a single large pump may draw down a dressing too fast, which may cause discomfort to the patient. "Draw down" or "drawing down a dressing" may refer to the process of providing negative pressure to a tissue site covered by a dressing until the pressure at the dressing drops from atmospheric pressure to the therapy pressure, e.g., −75 mm Hg. During the draw down process, a caregiver may be required to remain close to the patient to ensure that excess pressure is not applied to the tissue site. A single large pump may also be significantly louder than a standard pump used in a negative-pressure source. The increased noise of the larger pump may cause irritation to the patient, decreasing the likelihood that negative-pressure therapy may be used. A single larger pump may also require more electric power to operate; consequently, negative-pressure sources having a single larger pump may still suffer from short battery life, or require that the negative-pressure source be connected to an electrical outlet. Additionally, if a negative-pressure source having a single larger pump fails, the negative pressure being applied to the tissue site would be lost which may jeopardize therapy and the healing of the wound.

These limitations may be overcome by providing a therapy system comprising two or more therapy units providing negative pressure and/or instillation fluids to a single dressing disposed at a tissue site that may include one or more wounds in order to increase the net fluid-removal capacity of the therapy system. Such a system provides the redundancy necessary for a caregiver to empty one canister, while the other canister continues to collect fluids from the tissue site and provides the increased fluid-removal capacity needed to treat a serious wound as described above. One example embodiment of such a therapy system, for example, is the therapy system 100 that includes the therapy units 101 and 102 that are fluidly coupled to the dressing 104 and can simultaneously evacuate the tissue site 103 disposed under dressing 104. In one example embodiment, the therapy system 100 may include a Y-connector to fluidly couple the two therapy units via a single connector to the dressing. In another example embodiment as shown in FIG. 1, the therapy units 101 and 102 may be coupled to separate connectors 121 and 122 that are spaced apart on the cover 108 of the dressing 104. For example, each of the connectors 121 and 122 can be positioned proximate opposite ends of the dressing 104.

Another advantage of using two or more therapy units to provide negative pressure to a single dressing and tissue site is that therapy units typically used for less serious wound therapy that are standard and readily available may be used rather than developing a new special-purpose therapy unit for the large wounds described above. However, if two standard therapy units were connected to a single dressing to achieve a substantially constant removal of fluids at a higher rate, the two therapy units would fight for control of the wound pressure (WP). When therapy commences, one therapy unit will finally dominate over the other with respect to both fluid removal and wound pressure delivery. Consequently, the therapy units 101 and 102 in one example embodiment are synchronized so that they are not both operating at the same time, but rather share the same duty of fluid removal and pressure delivery.

Figure 4A:
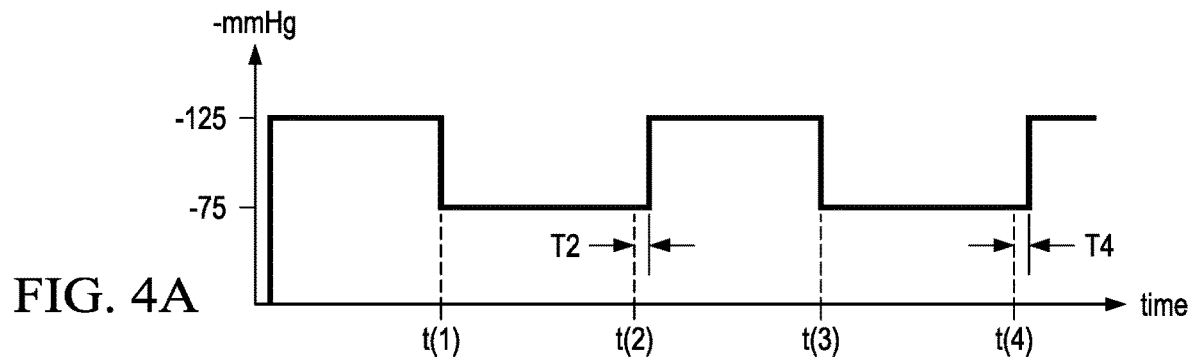
FIG. 4A is a graph illustrating an illustrative embodiment of a pressure control mode for the first therapy unit of FIG. 1 wherein the x-axis represents time in minutes (min) and/or seconds(sec) and the y-axis represents negative pressure generated by a pump in Torr (mmHg) that varies with time in an intermittent pressure mode that may be used for applying negative pressure in the therapy system.
Figure 4B:
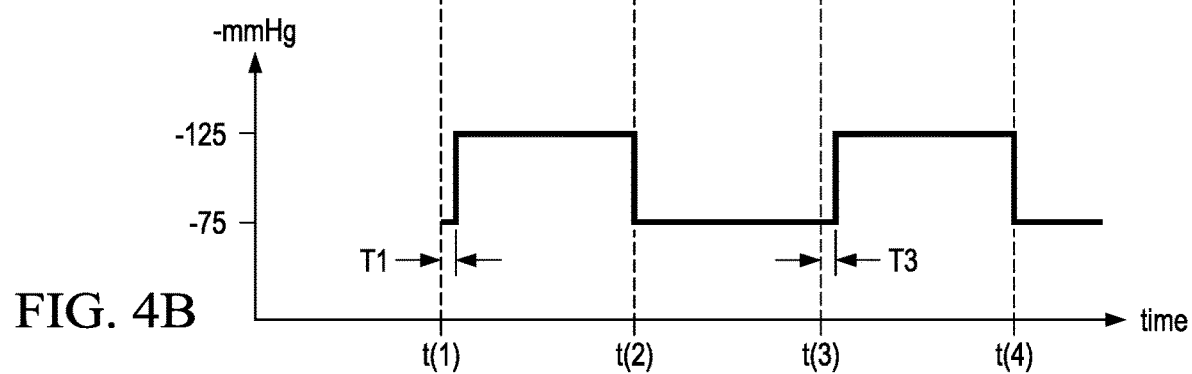
FIG. 4B is a graph illustrating an illustrative embodiment of a pressure control mode for the second therapy unit of FIG. 1 wherein the x-axis represents time in minutes (min) and/or seconds(sec) and the y-axis represents negative pressure generated by a pump in Torr (mmHg) that varies with time in an intermittent pressure mode that may be used for applying negative pressure in the therapy system.

In a first example embodiment, the user may configure the therapy units 101 and 102 to function in the intermittent pressure mode as described above and shown in FIG. 2A such that they both have the same period for the on-cycle and off-cycle time periods. Referring more specifically FIGS. 4A, 4B and 4C, the user may set the target pressure (TP) for both therapy units so that the wound pressure (WP) is cycled between the target pressure (TP) and atmospheric pressure. For example, the target pressure (TP) may be set by the user for each therapy unit at a negative pressure value of 125 mmHg for a specified period of time (e.g., 5 min) followed by the therapy being turned off for a specified period of time (e.g., 5 min) as shown in FIGS. 4A and 4B. The first therapy unit 101 may be activated first as shown in FIG. 4A by switching on the negative-pressure pump 131 to assert initial control of the wound pressure (WP) and initiate therapy. After the first on-cycle of the first therapy unit 101 expires at first time t(1) and the negative-pressure pump 131 is switched off, the user may activate the second therapy unit 102 as shown in FIG. 4B to take over the job of removing fluids by switching on the negative-pressure pump 132. After the first on-cycle of the second therapy unit 102 expires at second time t(2) and the negative pressure pump 132 is switched off, the first negative-pressure pump 132 is switched back on to reassert control over the wound pressure (WP) for a second on-cycle period.

Figure 4C:
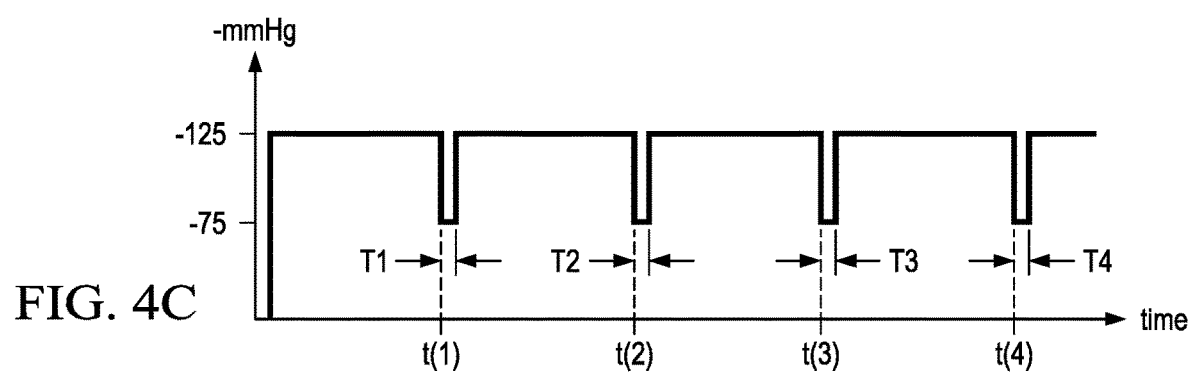
FIG. 4C is a graph illustrating an illustrative embodiment of the wound pressure (WP) being applied to the tissue site by the two therapy units of FIG. 1 wherein the x-axis represents time in minutes (min) and/or seconds (sec) and the y-axis represents negative pressure generated by a pump in Torr (mmHg) that varies with time in an intermittent pressure mode that may be used for applying negative pressure in the therapy system.

The cycle continues when the first negative-pressure pump 131 again switches off after its second on-cycle period expires at third time t(3) so that the second negative-pressure pump 132 switches back on for its on-cycle period which expires at fourth time t(4). FIG. 4C is a graph illustrating the wound pressure (WP) resulting from negative pressure being applied to the tissue site 103 by the first and second negative-pressure pumps 131 and 132 that varies with time in an intermittent pressure mode as just described. More specifically, the first therapy unit 101 is applying pressure and removing fluids for the first and third 5 minute periods, while the second therapy unit 102 is doing the same for the second and fourth 5 minute periods as shown in FIG. 4C.

In some embodiments of the intermittent pressure mode, the wound pressure (WP) is cycled between the target pressure (TP) and atmospheric pressure as described above. Additionally, some embodiments of the controllers being used in the therapy units are programmed to monitor the wound pressure (WP) during the off-cycle and provide an alarm or warning when the wound pressure (WP) cannot be lowered during the off-cycle. For example, this condition may occur when the first therapy unit 101 is switched off after the expiration of its on-cycle to begin its off-cycle, but the active controller senses that the wound pressure (WP) does not decay as a result of the second therapy unit 102 being activated and preventing the wound pressure (WP) from decaying. The first controller 137 of the first therapy unit 101 then senses that the wound pressure (WP) is still proximate the target pressure (TP) and cannot be lowered. Consequently, the first therapy unit 101 opens the release valve 135 to reduce the wound pressure (WP) and sets off an alarm because the wound pressure (WP) cannot be lowered, while the second therapy unit 102 has been activated by the user to apply negative pressure to the tissue site at the same time. In this example embodiment, the controllers 137 and 138 may be programmed to allow the user to deactivate the alarm and the release valves 135 and 136 when the user provides settings to the controllers 137 and 138 to recognize that two therapy units are being used to provide pressure to a single dressing. The controllers 137 and 138 may be programmed to inhibit the currently active therapy unit from setting off an alarm and opening the respective release valve when passing control over the wound pressure (WP) to the currently inactive therapy unit.

In one example embodiment, the controllers 137 and 138 also may be programmed to allow the user to set a minimum therapeutic pressure (MTP) that may be sensed by the currently inactive therapy unit while in its off-cycle to delay being switched on to its on-cycle to allow the negative wound pressure (WP) to drop from the target pressure (TP) after the currently active therapy unit is switched off. The minimum therapeutic pressure (MTP) may be sensed by the pressure sensors 117 and 118 and provided as feedback to the controllers 137 and 138. For example, the minimum therapeutic pressure (MTP) may be set at a negative pressure value of 75 mmHg so that when the first therapy unit 101 switches off the negative pressure pump 131 at first time t(1) and the wound pressure (WP) drops down to 75 mmHg after a first transition time period (T1), the second therapy unit 102 switches on so that the wound pressure (WP) remains substantially constant as shown in FIG. 4C. Correspondingly, when the second therapy unit 102 switches off the negative pressure pump 132 at second time t(2) and the wound pressure (WP) again drops down to 75 mmHg after a second transition time period (T2), the first therapy unit 101 switches back on so that the wound pressure (WP) again remains at a substantially constant pressure as shown in FIG. 4C. This cycle repeats itself when the first therapy unit 101 switches off at third time t(3) and the second therapy unit 102 switches on after a third transition time period (T3), and again when the second therapy unit 102 switches off at fourth time t(4) and the first therapy unit 101 switches on after a fourth transition time period (T4) to maintain a substantially constant wound pressure (WP) at the target pressure (TP) of 125 mmHg as shown in FIG. 4C.

As indicated above, the cover 108 of the dressing 104 may be attached and sealed to the tissue surrounding the tissue site 103, e.g. the peri-tissue. Various amounts of leakage may occur, for example, between peri-tissue and the cover 108 as a result of the cover 108 being improperly applied or being loosened during therapy. Although the dressing 104 is susceptible to leakage, the seal may be sufficiently strong so that the leakage rate of the wound pressure (WP) is minimal after the negative pressure pumps 131 and 132 are switched off as described above. Consequently, the wound pressure (WP) may not drop to the minimum therapy pressure (MTP) quickly enough after the negative pressure pumps 131 and 132 are switched off to trigger the inactive therapy unit to be switched on and begin providing negative pressure to the dressing 104 in order to maintain a substantially constant wound pressure (WP) proximate the target pressure (TP).

In one embodiment, for example, the controllers 137 and 138 may be programmed to recognize a minimum transition time period (MT) within which the inactive therapy unit must begin providing negative pressure after the active therapy unit is switched off. In one example embodiment, controllers 137 and 138 may utilize the pressure sensors 117 and 118 that may provide feedback to the controllers 137 and 138 to sense such a low leakage condition so that the wound pressure (WP) may be lowered by opening the release valves 135 and 136 to vent the therapeutic environment surrounding the tissue site 103 to the atmosphere. The controllers 137 and 138 would then close the release valves 135 and 136 after the wound pressure (WP) began lowering to the minimum therapeutic pressure (MTP) so that the inactive therapy unit can begin providing negative pressure to the dressing 104. For example, the controllers 137 and 138 may be programmed to open the release valves 135 and 136 to open and release the pressure at the tissue site 103 so that the wound pressure (WP) drops to a minimum therapy pressure (MTP) of 75 mmHg after a specific amount of time. Thus, the transition time periods, e.g., transition time periods T1, T2, T3 and T4, may all be set in the controllers 137 and 138 to be less than or equal to the minimum transition time period (MT). However, since the leakage rate may vary from cycle to cycle, the actual transition time period may also vary from one cycle to the next.

In another example embodiment, the controllers 137 and 138 also may be programmed to allow the user to set a switching pressure (SP) that may be sensed by the currently inactive therapy unit while in its off-cycle to switch the currently inactive therapy unit to its on-cycle when the negative wound pressure (WP) drops from the target pressure (TP) to the switching pressure (SP) after the currently active therapy unit is switched off. The switching pressure (SP) is greater than the minimum therapeutic pressure (MTP) so that switching from one controller to the other controller may be accomplished within a minimum transition time period (MT) in low leakage conditions without having to open the release valves 135 and 136 to vent the therapeutic environment surrounding the tissue site 103 to the atmosphere while waiting for the negative wound pressure (WP) to drop below the minimum therapeutic pressure (MTP). The switching pressure (SP) may be sensed by the pressure sensors 117 and 118 and provide an authorization signal to the controllers 137 and 138 as a feedback signal indicative of a wound pressure (WP) that drops below the switching pressure (SP), but not below the minimum therapeutic pressure (MTP).

For example, the switching pressure (SP) may be set at a negative pressure value less than or equal to 80% of the target pressure (TP) while the minimum therapeutic pressure (MTP) is set at a negative pressure value less than or equal to 50% of the target pressure (TP). The switching pressure (SP) also may be set at a negative pressure value less than or equal to 90% of the target pressure (TP) while the minimum therapeutic pressure (MTP) is set at a negative pressure value less than or equal to 50% of the target pressure (TP) to switch more quickly from one controller to the other controller under extreme low leakage conditions. However, since the leakage rate may vary from cycle to cycle, the switching pressure (SP) also may be programmed to vary from one cycle to the next. Consequently, when the first therapy unit 101 switches off the negative pressure pump 131 at first time t(1) and the wound pressure (WP) drops down to a value between the switching pressure (SP) and the minimum therapeutic pressure (MTP), the second therapy unit 102 switches on so that the wound pressure (WP) remains substantially constant as shown in FIG. 4C. Correspondingly, when the second therapy unit 102 switches off the negative pressure pump 132 at second time t(2) and the wound pressure (WP) again drops down to a value between the switching pressure (SP) and the minimum therapeutic pressure (MTP), the first therapy unit 101 switches back on so that the wound pressure (WP) again remains at a substantially constant pressure as shown in FIG. 4C. This cycle repeats itself when the first therapy unit 101 switches off at third time t(3) and the second therapy unit 102 switches on, and again when the second therapy unit 102 switches off at fourth time t(4) and the first therapy unit 101 switches on to maintain a substantially constant wound pressure (WP) at the target pressure (TP) of 125 mmHg as shown in FIG. 4C.

In operation, the therapy units 101 and 102 are pneumatically coupled to the tissue site 103 as described above and powered up by the user. In one example embodiment, each of the therapy units 101 and 102 may include a user interface (not shown) electrically coupled to the controllers 137 and 138, respectively, to provide output information to the user for the user to input information to the respective therapy unit. For example, the user may input information on the user interface indicating the presence of two or more therapy units and the order in which the therapy units are synchronized. For example, the therapy units 101 and 102 may be synchronized so that the first therapy unit 101 is activated first as a primary therapy unit followed by the second therapy unit 102 as a secondary therapy unit. In one example, the user may set the on-cycle and the off-cycle on the primary therapy unit for that device such as, for example, 5 minutes on and 5 minutes off as shown in FIGS. 4A and 4B. The secondary unit and any other devices may be programmed to receive information from the pressure sensor to monitor the wound pressure (WP) via the connector as described above in order to learn or copy the cycling settings that the user inputs to the user interface of the primary therapy unit. The user may input other information via the user interface including, for example, the target pressure (TP), the minimum therapeutic pressure (MTP), the switching pressure (SP) and the minimum transition time period (MT) as described above.

When the primary unit begins delivering negative pressure to the tissue site, the secondary unit monitors the wound pressure (WP) to detect when the wound pressure (WP) drops to the minimum therapy pressure (MTP) at the end of the first on-cycle as described above. When the primary unit has been running for 5 minutes, the release valve may be opened to reduce the wound pressure (WP) to the minimum therapy pressure (MTP) that may be, for example, set at 50% of the target pressure (TP). When the secondary unit senses that the wound pressure (WP) has reached at the minimum therapy pressure (MTP), the secondary unit activates its pump for another 5 minutes as a result of sensing that the primary therapy unit was providing a wound pressure (WP) at the target pressure (TP) for 5 minutes before being switched off. The primary therapy unit may then monitor the secondary therapy unit and wait until 5 minutes has expired to determine whether the wound pressure (WP) provided by the secondary therapy unit has again dropped to the minimum therapy pressure (MTP). When this occurs, the primary therapy unit again seizes control of the wound pressure (WP) to continue the cycle.

If either one of the therapy units which is the inactive therapy unit monitoring the active therapy unit senses a loss of wound pressure (WP) by an amount below the target pressure (TP) that is not acceptable or below the minimum therapy pressure (MTP) before completion of the on-cycle time period, e.g., 5 minutes, the inactive therapy unit may seize control of the wound pressure (WP) from the active therapy unit before the expiration of the on-cycle time period. This condition may occur, for example, when the canister of the currently active therapy unit has filled with fluids before the end of the current on-cycle time period.

If the secondary therapy unit is the inactive therapy unit monitoring the primary therapy unit and senses a wound pressure (WP) that drops to a pressure below the minimum therapy pressure (MTP) that is not acceptable, e.g., 25% of the target pressure (TP), the secondary therapy unit may seize control of the wound pressure (WP) from the active therapy unit as the primary therapy unit for only that on-cycle. The secondary therapy unit becomes the active therapy unit and may reset the on-cycle and off-cycle to a cycle duration time that is shorter, e.g., 2 minutes rather than 5 minutes, to allow the primary therapy unit to re-synchronize to the shorter cycle duration time and reacquire the status as the primary therapy unit. Resynchronization may occur for several cycles before the primary and secondary therapy units are again synchronized to deliver negative pressure to the tissue site. If the cycle duration time is too short, both canisters may be completely filled indicating the possibility of a bleed-out condition. The controllers may be programmed to provide an alarm indicative of this condition.

In yet another example embodiment of the therapy units, the controllers may be modified to include a multiple-device algorithm wherein each therapy unit is capable of detecting the presence of another therapy unit connected to the same dressing. For example, the controllers 137 and 138 may implement algorithms that utilize the release valves 135 and 136 for a purge cycle typically used in a continuous pressure mode to clear out any blockage that may form in the tubes 123 and 124, for example, between the canisters 115 and 116 and the connectors 121 and 122. In one embodiment, the purge cycle may be implemented every five minutes when the release valves 135 and 136 are opened momentarily for about one second to create a differential pressure between the dressing 104 and the environment with a burst of air flowing from the release valves 135 and 136 to the therapeutic space under the cover 108 of the dressing 104 and into the tubes 123 and 124 to hopefully to force out any blockage into the canisters 115 and 116. If the purge cycle has a duration of about one second, it would be desirable that the controllers 137 and 138 sample the pressure sensors 117 and 118 at a sampling rate in the range of approximately 2-100 samples per second in one example embodiment, and a nominal sampling rate of about 10 samples per second in order to improve the fidelity of the multiple-device algorithm.

Figure 5:
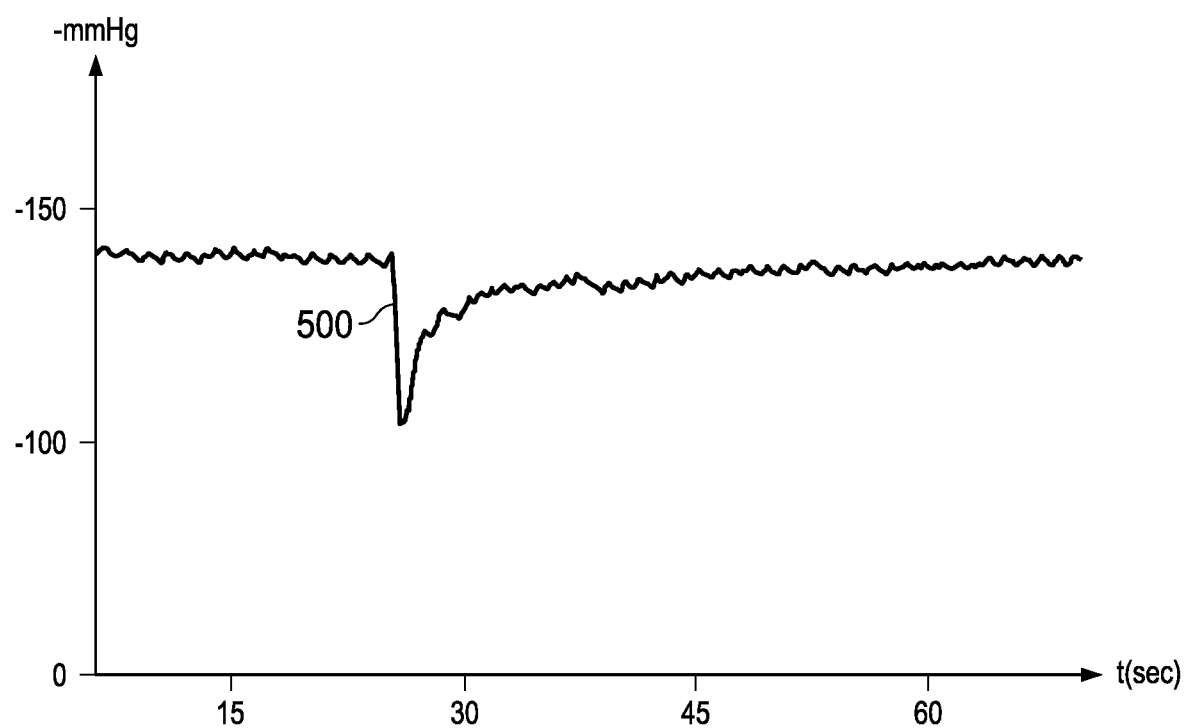
FIG. 5 is a graph illustrating a waveform of the wound pressure (WP) responsive to the removal of negative pressure from the tissue site and the re-application of negative pressure to the tissue site by only one therapy unit of FIG. 1 that is fluidly coupled to the manifold, wherein the x-axis represents time in minutes (min) and/or seconds(sec) and the y-axis represents negative pressure generated by a pump in Torr (mmHg) that varies with time in a continuous pressure mode of operation.
Figure 6A:
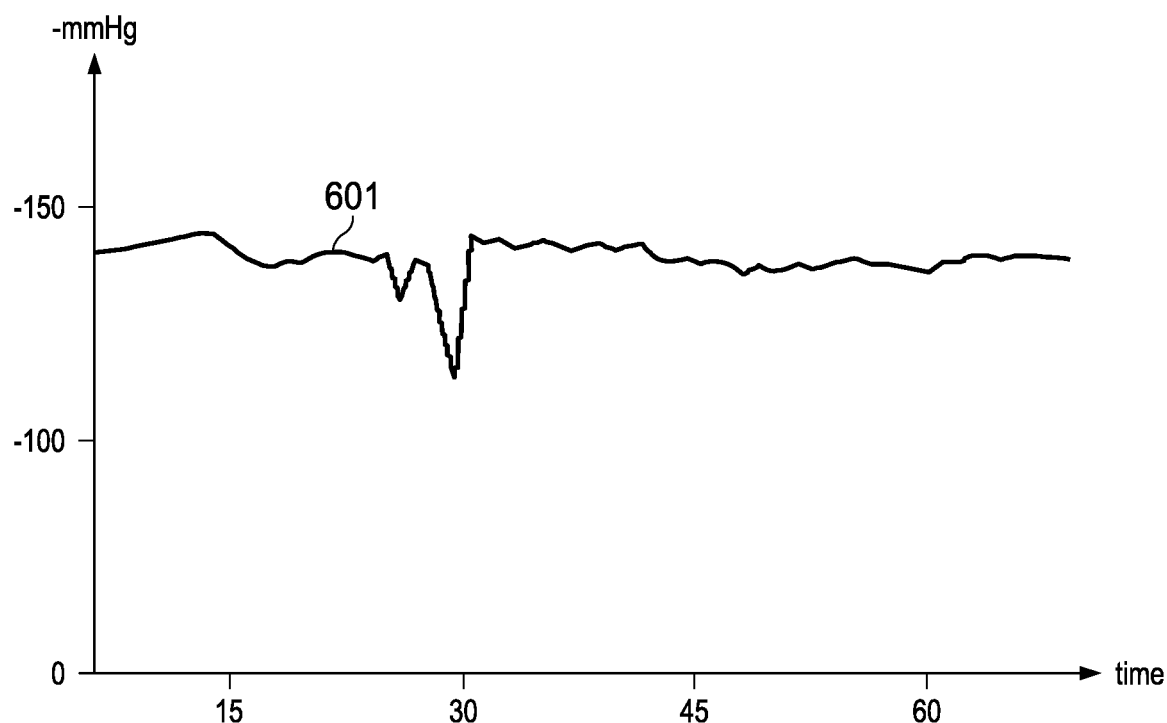
FIG. 6 is a graph illustrating a waveform of the wound pressure (WP) responsive to the removal of negative pressure from the tissue site and the re-application of negative pressure to the tissue site by both of the therapy units of FIG. 1 that are fluidly coupled to the manifold, wherein the x-axis represents time in minutes (min) and/or seconds(sec) and the y-axis represents negative pressure generated by a pump in Torr (mmHg) that varies with time in an intermittent pressure mode of operation.
Figure 6B:
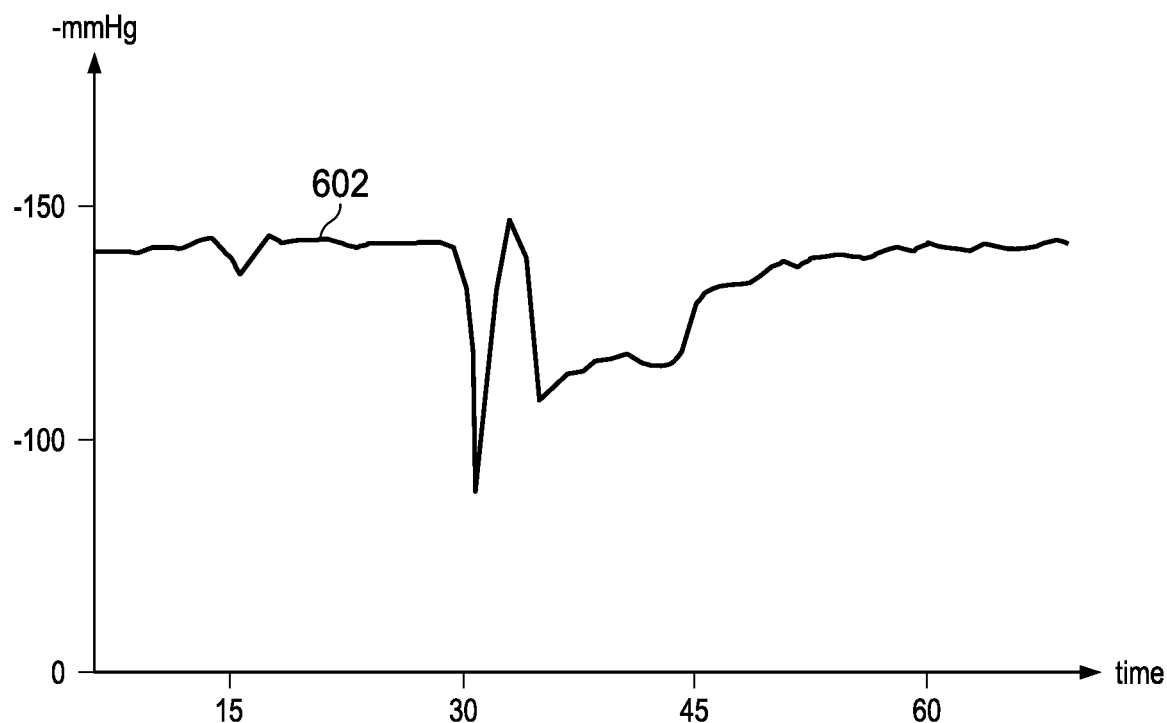

When using a single therapy unit, the wound pressure (WP) has a characteristic first-order response wherein the wound pressure (WP) momentarily becomes less negative, e.g., 100 mmHg, when the release valves 135 and 136 are opened during the purge cycle, but quickly return to the target pressure (TP) set by the user, e.g., 125 mmHg. The multiple-device algorithm may detect a first-order response such as, for example, a first-order waveform 500 as shown in FIG. 5 which can also be characterized as a simple negative pressure spike dropping from the set target pressure (TP) to a nominal less negative value with a rapid return to the set target pressure (TP). However, if a second therapy unit is connected to the same dressing, waveforms other than the characteristic first-order waveform have been observed indicating the presence of a second therapy unit. For example, double-spike pressure waveforms have been observed that do not correspond to the operation of a single therapy unit such as, for example, double-spike pressure waveforms 601 and 602 in FIG. 6. Therefore, in one embodiment of the multi-device algorithm, the presence of a second therapy unit may be detected by virtue of the absence of the characteristic first-order waveform. In another example embodiment of the multi-device algorithm, the presence of a second therapy unit may be detected by identifying a specific waveform that is different from the characteristic first-order waveform such as, for example, double-spike pressure waveforms 601 and 602 in FIG. 6. In yet another example embodiment of the multi-device algorithm, the presence of a second therapy unit may be detected by comparing the measured pressure with the characteristic first-order waveform and identifying any deviations with further processing of the waveform.

The structure and functioning of the multiple-device algorithm as described above does not need to be limited to the purging cycle, but may be implemented separately from or in lieu of the purging cycle in the intermittent pressure mode. For example, the multiple-device algorithm may be implemented at the end of the on-cycle of the active therapy unit when the pump is switched off and the release valve is opened momentarily so that the multiple-device algorithm may sample the wound pressure (WP) during the transition time period (T) as described above to determine whether the waveform of the sampled wound pressures (WP) is a first-order waveform. If the waveform is not a first-order waveform, the controller provides an indication to the user that another therapy unit is fluidly coupled to the same dressing as described above. Additionally, the multiple-device algorithm may monitor the therapy system over an extended period of time, e.g., an hour or more, in order to detect atypical pressure waveforms or deviations from the characteristic first-order waveforms which do not necessarily occur with every cycle. The multiple-device algorithm also may be implemented to synchronize the operating cycles of the therapy units, i.e., the transition time periods (T) between the on-cycles and the off-cycles. The multiple-device algorithm also may be implemented to ascertain the leakage rate of the dressing which affects the transition time periods (T) of the wound pressure (WP) back to the target pressure (TP) after opening and closing the release valves.

The systems, apparatuses, and methods described herein may provide significant advantages. For example, two therapy units designed for general usage for treating tissue sites may be combined to provide negative pressure wound therapy to a wound requiring large volumes of fluid to be managed by a therapy system. The same two therapy units may be synchronized as described above so that a clinician is not required to manage treatment on-site, but rather can do so remotely. Continuous negative pressure treatment can be maintained at a substantially constant negative pressure by one therapy unit while the canister of the other therapy unit is being emptied. The dual therapy unit embodiment may also provide installation therapy wherein one of the therapy units delivers fluids while the other therapy unit removes the installation fluids and removes exudates from the tissue site.

While shown in a few illustrative embodiments, a person having ordinary skill in the art will recognize that the systems, apparatuses, and methods described herein are susceptible to various changes and modifications. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 104, the canisters 115 and 116, or both may be eliminated or separated from other components for manufacture or sale. In other example configurations, the controllers 137 and 138 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. A system for treating a tissue site, comprising:
   a first therapy unit comprising a first pump and a first controller;
   a second therapy unit comprising a second pump and a second controller;
   a tissue interface fluidly coupled to the first pump and the second pump;
   a cover adapted to provide a fluid seal between a therapeutic environment including the tissue site and the tissue interface on one side of the cover and a local external environment the other side of the cover; and
   wherein the first controller and the second controller are adapted to operate in an intermittent pressure mode to switch the first therapy unit and the second therapy unit on and off between an active state and an inactive state to activate either one of the first pump and the second pump in the active state and deactivate the other one of the first pump and the second pump in the inactive state to provide substantially constant treatment to the tissue interface within the therapeutic environment.

2. The system of claim 1, wherein the first pump and the second pump are both negative pressure pumps adapted to provide negative pressure to the tissue interface within the therapeutic environment.

3. The system of claim 1, wherein the first pump is a negative pressure pump adapted to provide negative pressure to the tissue interface within the therapeutic environment and the second pump a positive pressure pump adapted to provide liquids to the tissue interface within the therapeutic environment.

4. The system of claim 1, wherein the first pump and the second pump are fluidly coupled to the tissue interface at separate locations on the tissue interface.

5. The system of claim 1, wherein the first therapy unit further comprises a first pressure sensor fluidly coupled to the therapeutic environment and electrically coupled to the first controller and the second therapy unit further comprises a second pressure sensor fluidly coupled to the therapeutic environment and electrically coupled to the second controller.

6. The system of claim 5, wherein the first pressure sensor and the second pressure sensor are adapted to sense a wound pressure (WP) within the therapeutic environment and provide pressure signals indicative of the wound pressure (WP) to a corresponding one of the first and second controllers.

7. The system of claim 6, wherein the first controller and the second controller are further adapted to operate either one of the first and second pumps when in the active state to provide a wound pressure (WP) proximate a target pressure (TP).

8. The system of claim 7, wherein the first controller and the second controller are further adapted to detect a wound pressure (WP) proximate a switching pressure (SP) that is less than the target pressure (TP).

9. The system of claim 8, wherein the first controller and the second controller are further adapted to switch on a corresponding one of the first pump and the second pump from the inactive state to the active state when a corresponding one of the first controller and the second controller receives an authorization signal indicative of a wound pressure (WP) that drops below the switching pressure (SP).

10. The system of claim 9, wherein the switching pressure (SP) is less than or equal to 80% of the target pressure (TP).

11. The system of claim 9, wherein the switching pressure (SP) is less than or equal to 90% of the target pressure (TP).

12. The system of claim 8, wherein the first controller and the second controller are further adapted to detect a wound pressure (WP) proximate a minimum therapeutic pressure (MTP) less than the switching pressure (SP).

13. The system of claim 12, wherein the first controller and the second controller are further adapted to switch on a corresponding one of the first pump and the second pump from the inactive state to the active state when a corresponding one of the first controller and the second controller receives an authorization signal indicative of a wound pressure (WP) between the switching pressure (SP) and the minimum therapeutic pressure (MTP).

14. The system of claim 13, wherein the switching pressure (SP) is less than or equal to 80% of the target pressure (TP) and wherein the minimum therapeutic pressure (MTP) is less than or equal to 50% of the target pressure (TP).

15. The system of claim 13, wherein the switching pressure (SP) is less than or equal to 90% of the target pressure (TP) and wherein the minimum therapeutic pressure (MTP) is less than or equal to 50% of the target pressure (TP).

16. A system for treating a tissue site, comprising:
   a first therapy unit comprising a first controller and a first pump for providing negative pressure;
   a second therapy unit comprising a second controller and a second pump for providing negative pressure;
   a manifold fluidly coupled to the first pump and the second pump;
   a cover adapted to provide a fluid seal between a therapeutic environment including the tissue site and the manifold for receiving the negative pressure on one side of the cover and a local external environment the other side of the cover; and
   wherein the first controller and the second controller are adapted to switch off either one of the first pump and the second pump from a currently active state during an on-cycle and provide an authorization signal after being switched off in response to a reduction of negative pressure in the therapeutic environment while the other one of the first pump and the second pump is in a currently inactive state during an off-cycle.

17. The system of claim 16, wherein the first controller and the second controller are further adapted to switch on the other one of the first pump and the second pump from the currently inactive state to the currently active state in response to detection of the authorization signal.

18. The system of claim 17, wherein the first therapy unit further comprises a first pressure sensor and the second therapy unit further comprises a second pressure sensor fluidly, and wherein both the first pressure sensor and the second pressure sensor are coupled to the therapeutic environment and adapted to sense the negative pressure within the therapeutic environment.

19. The system of claim 18, wherein the first controller and the second controller are further adapted to operate either one of the first and second pumps when in the currently active state to provide negative pressure proximate a target pressure (TP).

20. The system of claim 19, wherein the first controller and the second controller are further adapted to detect a negative pressure in the therapeutic environment proximate a switching pressure (SP) that is less than the target pressure (TP).

21. The system of claim 20, wherein the first controller and the second controller are further adapted to switch on a corresponding one of the first pump and the second pump from the currently inactive state to the currently active state when a corresponding one of the first controller and the second controller receives an authorization signal wherein the reduction of negative pressure drops to a value below the switching pressure (SP).

22. The system of claim 20, wherein the first controller and the second controller are further adapted to detect a negative pressure in the therapeutic environment proximate a minimum therapeutic pressure (MTP) less than the switching pressure (SP).

23. The system of claim 22, wherein the first controller and the second controller are further adapted to switch on a corresponding one of the first pump and the second pump from the currently inactive state to the currently active state when a corresponding one of the first controller and the second controller receives an authorization signal wherein the reduction of negative pressure drops to a value between the switching pressure (SP) and the minimum therapeutic pressure (MTP).

24. The system of claim 16, wherein the on-cycles of the first pump and the second pump have substantially the same duration.

25. The system of claim 16, wherein the off-cycles of the first pump and the second pump have substantially the same duration.

26. The system of claim 16, wherein the on-cycles of the first pump and the second pump and the off-cycles of the first pump and the second pump have substantially the same duration.

27. The system of claim 16, wherein the first controller and the second controller are further adapted to operate either one of the first and second pumps when in the currently active state to provide negative pressure to the therapeutic environment proximate a target pressure (TP).

28. The system of claim 27, wherein each of the first therapy unit and the second therapy unit further comprises a release valve fluidly coupling the therapeutic environment to the local external environment.

29. The system of claim 28, wherein each of the first controller and the second controller is adapted to open the corresponding the release valve after completion of an on-cycle to reduce the negative pressure being applied to the therapeutic environment to a switching pressure (SP) that is less than the target pressure (TP).

30. The system of claim 29, wherein the switching pressure (SP) is less than or equal to 80% of the target pressure (TP).

31. The system of claim 29, wherein the switching pressure (SP) is less than or equal to 90% of the target pressure (TP).

32. The system of claim 29, wherein either one of the first controller and the second controller in the currently inactive state monitors the applied negative pressure and turns on the corresponding one of the first and second pumps to commence providing negative pressure in the active state when the applied negative pressure is less than or equal to the switching pressure (SP).

33. The system of claim 29, wherein each of the first controller and the second controller is further adapted to open the corresponding the release valve after completion of an on-cycle to reduce the negative pressure being applied to the therapeutic environment to a minimum therapeutic pressure (MTP) that is a value less than the switching pressure (SP).

34. The system of claim 33, wherein either one of the first controller and the second controller in the currently inactive state monitors the applied negative pressure and turns on the corresponding one of the first and second pumps to commence providing negative pressure in the active state when the applied negative pressure is a value between the switching pressure (SP) and the minimum therapeutic pressure (MTP).

35. The system of claim 33, wherein the switching pressure (SP) is less than or equal to 80% of the target pressure (TP) and wherein the minimum therapeutic pressure (MTP) is less than or equal to 50% of the target pressure (TP).

36. The system of claim 33, wherein the switching pressure (SP) is less than or equal to 80% of the target pressure (TP) and wherein the minimum therapeutic pressure (MTP) is less than or equal to 25% of the target pressure (TP).

37. The system of claim 33, wherein the switching pressure (SP) is less than or equal to 90% of the target pressure (TP) and wherein the minimum therapeutic pressure (MTP) is less than or equal to 50% of the target pressure (TP).

38. The system of claim 33, wherein the switching pressure (SP) is less than or equal to 90% of the target pressure (TP) and wherein the minimum therapeutic pressure (MTP) is less than or equal to 25% of the target pressure (TP).

39. The system of claim 16, wherein each of the first controller and the second controller is operable to provide a synchronization order for the first and second therapy devices to determine the sequence of turning on the first pump and the second pump.

40. A method for treating a tissue site, comprising:
positioning a manifold at a tissue site;
fluidly coupling a first pump of a first therapy unit to the manifold, wherein the first therapy unit includes a first controller;
fluidly coupling a second pump of a second therapy unit to the manifold, wherein the second therapy unit includes a second controller;
covering the manifold with a cover to provide a fluid seal between a therapeutic environment including the tissue site and the manifold on one side of the cover and a local external environment the other side of the cover;
synchronizing operation of the first therapy unit so that the first pump is turned on only when the second pump is turned off; and
synchronizing operation of the second therapy unit so that the second pump is turned on only when the first pump is turned off.

* * * * *